United States Patent
Bergmann et al.

(10) Patent No.: US 8,524,463 B2
(45) Date of Patent: Sep. 3, 2013

(54) DIAGNOSIS AND RISK CLASSIFICATION OF ACUTE CORONARY SYNDROME BY MEANS OF CT-PROET-1 IN COMBINATION WITH NT-PROBNP

(75) Inventors: Andreas Bergmann, Berlin (DE); Nils Morgenthaler, Berlin (DE); Jana Papassotiriou, Berlin (DE); Joachim Struck, Berlin (DE); Leong L. Ng, Leicester (GB)

(73) Assignee: B.R.A.H.M.S GmbH, Henningsdorf (DE)

( * ) Notice: Subject to any disclaimer, the term of this patent is extended or adjusted under 35 U.S.C. 154(b) by 784 days.

(21) Appl. No.: 12/520,166

(22) PCT Filed: Dec. 22, 2007

(86) PCT No.: PCT/DE2007/002313
§ 371 (c)(1),
(2), (4) Date: Sep. 18, 2009

(87) PCT Pub. No.: WO2008/077396
PCT Pub. Date: Jul. 3, 2008

(65) Prior Publication Data
US 2010/0151504 A1    Jun. 17, 2010

(30) Foreign Application Priority Data
Dec. 22, 2006 (DE) .......... 10 2006 060 835

(51) Int. Cl.
*G01N 31/00* (2006.01)
*G01N 33/53* (2006.01)

(52) U.S. Cl.
USPC ........ 435/7.21; 435/7.1; 435/287.9; 436/501; 436/518; 422/50; 422/430; 424/9.1; 424/520; 530/300; 530/350

(58) Field of Classification Search
None
See application file for complete search history.

(56) References Cited

U.S. PATENT DOCUMENTS
2008/0026414 A1    1/2008   Bergmann et al.

FOREIGN PATENT DOCUMENTS
| | | |
|---|---|---|
| CA | 2428760 A1 | 11/2003 |
| EP | 1363128 A2 | 11/2003 |
| EP | 1619505 A2 | 1/2006 |
| WO | WO-2004/046729 | 6/2004 |
| WO | WO-2005/078456 A1 | 8/2005 |

OTHER PUBLICATIONS

Khan, Sohail Q. et al., "C-terminal pro-endothelin-1 offers additional prognostic information in patients after acute myocardial infarction: Leicester Acute Myocardial Infarction Peptide (LAMP) Study", American Heart Journal, vol. 154, No. 4, pp. 736-742, Oct. 2007.

*Primary Examiner* — Lisa Cook
(74) *Attorney, Agent, or Firm* — Novak Druce Connolly Bove + Quigg LLP (57) ABSTRACT

The invention relates to a method for diagnosis and/or risk classification for acute coronary syndrome (ACS), in particular for acute myocardial infarct (AMI) and angina pectoris (AP) and/or a post-myocardial infarct, wherein a determination of the C-terminal pro-endothelin (CT-proET-1) or fragments and partial peptides therefrom, is carried out in combination with NT-proBNP.

20 Claims, 4 Drawing Sheets

DIAGNOSIS AND RISK CLASSIFICATION OF ACUTE CORONARY SYNDROME BY MEANS OF CT-PROET-1 IN COMBINATION WITH NT-PROBNP

RELATED APPLICATIONS

This application is a national stage application (under 35 U.S.C. §371) of PCT/DE2007/002313, filed Dec. 22, 2007, which claims benefit of German application 102006060835.6, filed Dec. 22, 2006.

The invention relates to a method for diagnosis and/or risk classification of acute coronary syndrome (ACS), particularly of acute myocardial infarction (post-AMI), wherein a determination of the C-terminal pro-endothelin (CP-proET-1) or fragments and partial peptides thereof, is carried out in combination with NT-proBNP.

The risk classification has an increasing importance in the area of heart diseases, whether in symptomatic or asymptomatic patients. Particularly in the area of acute coronary syndrome (ACS) and acute myocardial infarction (AMI) and Angina pectoris (AP), as well as post-myocardial infarction (post-AMI) there is a high demand for a suitable risk classification.

A suitable therapy requires early diagnosis and differentiation of acute coronary syndrome already in the emergency room in connection with the necessity to make clinical decisions. Due to unspecified symptoms (chest pain) in acute coronary syndrome, both differentiation and delimitation of other illnesses and the recognizing of acute coronary syndrome are essential. This is also necessary in the case of post-myocardial infract.

Biochemical markers—particularly the classics, such as cardial troponin, myoglobin, and CK-MB-mass—have been carried out in prior art for the prognosis of a myocardial infarction (Katus, N. A.; Remppis, A.; Scheffold, T.; Diederich, K. W. and Kuebler, W (1991): Intracellular compartmentation of cardiac troponin T and its release kinetics in patients with reperfused and nonreperfused myocardial infarction, Am J Cardio 67 (16): 1360-1367). The B-type of natriuretic peptide (BNP) together with pro-BNP, NT-proBP (EP1363128B1, EP1666881A2 has proven to be a further effective biochemical marker in myocardial diagnostics.

The C-terminal pro-endothelin fragments (CT-pro-ET-1) together with the amino acid sequences 93-212 or 168-212 of the pepro-endothelin (SEQ ID No. 1) is described in EP 1564558 for the diagnosis of cardio vascular diseases for the indirect determination of the endothelin-1 or the big endothelin-1 content. Furthermore, it is known from EP 1564558 B1 that cardial parameters, such as ANP, BNP and proBNP may be utilized in cardial diagnostics for multi-parameter diagnostics.

One disadvantage of the known diagnosing method utilizing the currently known markers, however, is that a premature and complete determination of risk patients is not sufficiently successful. One object based on the invention is therefore to develop a method for risk classification of acute coronary syndrome and post-myocardial infarction, which enables an improved determination of risk patients.

Another disadvantage is that according to prior art often no sufficient sensitivity and/or specificity of the markers is obtained.

Another object is to provide a method for risk classification of acute coronary syndrome and post-myocardial infarction, wherein at least one marker, or a combination of markers, has a sufficient sensitivity and specificity in an in-vitro diagnosis.

It is therefore the task of the present invention to provide a method for diagnosis and/or risk classification of acute coronary syndrome and post-myocardial infarction.

The task is solved by a method for diagnosis and risk classification of acute coronary syndrome and post-myocardial infarction, wherein a determination of the CT-proET-1 is carried out with the free fragments (SEQ ID No. 2 and/or SEQ ID No. 3) (in short: "CT-proET-1"), or fragments and partial peptides thereof, in combination with NT-proBNP (SEQ ID No. 4) (hereinafter referred to as the method according to the invention).

Surprisingly CT-proET-1 or fragments and partial peptides thereof, in combination with NT-proBNP, have a high sensitivity and specificity for the diagnosis of acute coronary syndrome and post-myocardial infarction (see examples and figures).

The term "acute coronary syndrome" comprises different phases of coronary heart disease, which are a direct threat to life. This particularly applies to emergency medicine, in fact an acute myocardial infarction and/or Angina pectoris and sudden cardiac death. In addition to acute myocardial infarction, which is defined according to WHO criteria (WHO (1979): Nomenclature and criteria for diagnosis of ischemic heart disease. Report of the Joint International Society and Federation of Cardiology/World Health Organization task force on standardization of clinical nomenclature, Circulation 59 (3): 607-609), as an acute chest pain event lasting more than 20 minutes, combined with elevations of the ST segment and/or an increase of myocardial enzymes, the term of instable Angina pectoris (AP) was stamped out, which is found in literature according to the invention under "acute coronary syndrome" (Hamm C W: Guidelines: Acute coronary syndrome (ACS)—Part 1: ACS without persisting elevation of ST segment. Z Kardiol (2004) 93:72-90; also see: Pschyrembel, De Gruyter, Berlin 2004).

"Disadvantageous (negative) event in post-myocardial infarction patients," particularly means a further (subsequent) myocardial infarction, coronary failure, or death, or other worsening of the prognosis of the patient in the course of this invention.

"Myocardial infarction" (heart attack, AMI (acute myocardial infarction)) means an acute and life-threatening disease of the heart in the course of this invention, wherein the dying off or the tissue necrosis of parts of the heart muscle (myocard) occurs due to a circulatory disorder (ischemia), which usually lasts longer than 20 minutes. The main symptom of a heart attack is a suddenly occurring, mostly strong pain in the chest region ("chest pain") lasting more than 20 minutes, which may radiate to the shoulders, arms, lower jaw, and upper abdomen, and may be accompanied by sweating, nausea, and possibly vomiting. Coronary failure is possible due to a myocardial infarction.

The term "post-myocardial infarction" means that a patient has already suffered from a myocardial infarction in the past, e.g., for example, for more than 1 hour, particularly for 20 hours, particularly for 1 to 5 days or for 3 to 5 days, and now lives in the post ("after") phase, and has suffered no direct death, but a further disadvantageous event can be directly or indirectly expected.

All stated indications are further described, for example, in Pschyrembel, De Gruyter, Berlin 2004.

The term "risk classification" comprises the worse prognosis in patients, particularly emergency room patients and risk patients, for the purpose of more intensive diagnostics and therapy/treatment of acute coronary syndrome, particularly myocardial infarction, Angina pectoris, and/or post-myocardial infarction with the goal of enabling a course that is as favorable as possible. A risk classification according to the invention allows in succession an effective treatment process that is appropriate with acute coronary syndrome utilizing the percutaneous coronary interventions and the newer pharmaceuticals.

The invention therefore also relates to identifying patients having an increased risk and/or an unfavorable prognosis of acute coronary syndrome, particularly myocardial infarction, Angina pectoris, and/or post-myocardial infarction, especially in symptomatic and/or asymptomatic patients, particularly in emergency room patients.

A safe classification may occur particularly advantageously especially in cases of emergency and/or intensive medicine by means of the method according to the invention. The method according to the invention thus enables clinical decisions, which lead to a quick therapy success and to avoiding death. Such clinical decisions also comprise continuative treatments by means of pharmaceuticals for the treatment or therapy of acute coronary syndrome, particularly myocardial infarction (AMI) and of Angina pectoris (AP) and/or post-myocardial infarction.

Therefore, the invention also relates to a method for the diagnosis and/or risk classification of patients having acute coronary syndrome and/or post-myocardial infarction for carrying out clinical decisions, such as the continuative treatment and therapy by means of pharmaceuticals, preferably in the chronologically critical intensive medicine or emergency medicine, including the decision of hospitalization of the patient.

In a further preferred embodiment the method according to the invention therefore relates to the therapy control of acute coronary syndrome, particularly myocardial infarction (AMI), and Angina pectoris (AP), as well as post-myocardial infarction.

In a further preferred embodiment of the method according to the invention the diagnosis and/or risk classification for the prognosis, differential diagnostic early detection and recognition, assessment of the degree of severity, and therapy-accompanying assessment of the course takes place.

In a further preferred embodiment the invention relates to a method for in-vitro diagnostics for an early or differential diagnosis or prognosis of acute coronary syndrome, or myocardial infarction, or Angina pectoris, and/or post-myocardial infarction, wherein a determination of the marker CT-proET-1 or fragments and partial peptides thereof is carried out in combination with NT-proBNP on a patient to be examined.

The invention further relates to a method for the diagnosis and risk classification of acute coronary syndrome, or a method for the early or differential diagnosis or prognosis of acute coronary syndrome, particularly myocardial infarction or Angina pectoris and/or post-myocardial infarction according to one of the embodiments stated above, wherein after the onset of the symptoms the cut-off values (threshold values) for the combination of CT-proET-1 or fragments and partial peptides thereof with NT-proBNP are 80-150 pmol/l, particularly 90-130 pmol/l, particularly 109.5 pmol/l for CT-proET-1 and 750-1100 pmol/l, particularly 800-950 pmol/l, particularly 827.2 pmol/l for NT-proBNP at a maximum of sensitivity and specificity (see FIGS. 3 and 4) for the diagnosis and/or risk classification in the stated embodiments.

Based upon the same said method according to the invention is advantageously sensitive and specific.

In one embodiment of the method according to the invention body fluid, preferably blood, is drawn from the patient to be examined, optionally full blood or serum, or available plasma, and the diagnosis is carried out in vitro/ex vivo, e.g. outside of the human or animal body. Based on the determination of the marker CT-proET-1 or fragments and partial peptides thereof, in combination with NT-proBNP, a high sensitivity and specificity for acute coronary syndrome, myocardial infarction, and Angina pectoris and/or post-myocardial infarction is obtained, and the diagnosis or risk classification can then be carried out based on the amount present in at least one patient sample.

"CT-proET-1" means a human protein or polypeptide in the course of this invention, which can be obtained from the preproendothelin, and in the course of the preproendothelin (SEQ ID No. 1) comprise the free fragments having the amino acids 93-212 (129 AS, SEQ ID No. 2: ALENLLPT KATDRENRCI CASQKDKKCW NFCQAGKELR AEDIMEKDWN NHKKGKDCSK LGKKCIYQQL VRGRKIRRSS EEHLRQTRSE TMRNSVKSSF HDPKLKGKPS RERYVTHNRA HW), or having the amino acids 168-212 (44AS, SEQ ID No. 3: RSS EEHLRQTRSE TMRNSVKSSF HDPKLKGKPS RERYVTHNRA HW, also see Figure), and also the fragments or partial peptides available from the same. Said polypeptides according to the invention may also have post-translational modifications, such as glycolization, lip(o)lidation, or derivatizations.

"NT-proBNP" in the course of this invention means the N-terminal pro-hormone of the B-type of a natriuretic peptide, a human protein, or polypeptide, having the amino acid sequence according to SEQ ID No. 4 (76 AS: HPLG SPGSASDLET SGLQEQRNHL QGKLSELQVE QTSLEPLQES PRPTGVWKSR EVATEGIRGH RKMVLYTLRA PR).

In another embodiment the determination of CT-proET-1 or fragments and partial peptides thereof, in combination with NT-proBNP, may additionally be carried out with further markers, in fact such markers, which already indicate an acute coronary syndrome, particularly myocardial infarction, or Angina pectoris, as well as post-myocardial infarction.

Therefore, the invention relates to such an embodiment of the method according to the invention, wherein in addition to the combination according to the invention, the determination is carried out with at least one further marker, which is selected from the group of inflammatory markers, cardiovascular markers, neurohormonal markers, or ischemic markers on a patient to be examined.

According to the invention the inflammatory marker may be selected from at least one marker of the group of C-reactive protein (CRP), cytokines, such as TNF-alpha, interleukins, such as IL-6, procaicitonine (1-116, 3-116), and adhesion molecules, such as VCAM or ICAM, and the cardiovascular marker from markers particularly indicating a necrosis of the myocardial tissue, and markers having an influence on the blood pressure, selected from at least one marker from the group of creatine kinasis, myoglobin, myeloperoxidasis, further natriuretic protein, particularly ANP (or ANF), proANP, NT-proANP, BNP, proBNP, or a partial sequence thereof, cardial troponin, CRP. Furthermore, these also mean circulation regulating (pro)hormones, particularly pro-gastrin releasing peptide (proGRP), pro-leptin, pro-neuropeptide-Y, pro-somatostatin, pro-neuropeptide-YY, pro-opiomelanocortin, or pro-adrenomed din (proADM), or a partial sequence thereof.

The ischemic marker may be selected from at least one marker from the group of troponin I and T, CK-MB. Furthermore, the neurohormonal marker may be at least one further natriuretic protein, particularly ANP (or ANF), proANP, NT-proANP, BNP, proBNP, or a partial sequence thereof.

In a further embodiment of the invention the method according to the invention may be carried out within the course of an in-vitro diagnosis by means of parallel or simultaneous determinations of the markers (i.e. multi-titer plates having 96 or more cavities), wherein the determinations are carried out on at least one patient sample.

Furthermore the method according to the invention and the determinations thereof may be carried out in a diagnostic device by means of an automatic analysis device, particularly by means of a Kryptor (http://www.kryptor.net/).

In a further embodiment the method according to the invention and the determinations thereof may be carried out by means of a quick test (i.e. lateral-flow test or point-of care), whether single or multiple parameter determination. A particularly preferred embodiment is a self-test, or a device suitable for emergency diagnostics.

Furthermore the invention relates to the use of CT-proET-1 or fragments and partial peptides thereof, in combination with NT-proBNP for risk classification of acute coronary syndrome, myocardial infarction, or Angina pectoris and/or post-myocardial infarction and/or for in-vitro diagnostics for the early or differential diagnosis or prognosis of acute coronary syndrome, myocardial infarction, or Angina pectoris and/or post-myocardial infarction.

A further object is providing a respective diagnostic device, or the use thereof for carrying out the method according to the invention.

In the course of this invention such a diagnostic device is an array, or assay (such as immune assay, ELISA, etc.), a device for carrying out the method according to the invention in the furthest sense.

The invention also refers to a kit for the diagnosis and/or risk classification of acute coronary syndrome, myocardial infarction, and/or Angina pectoris, and/or post-myocardial infarction, containing detection reagents for determining CT-proET-1 or fragments and partial peptides thereof, in combination with NT-proBNP, and optionally further markers stated above. Such detection reagents comprise, for example, antibodies, etc.

The following examples and figures serve for explaining the invention in further detail, however, without limiting the invention to said examples and figures.

EXAMPLES AND FIGURES

Example 1

A blood sample was taken from 983 patients, who were introduced in the emergency room of a hospital as having the heart attack related main symptom of chest pain, The patients were observed for a median period of 342 days, wherein 10.3% of the patients died, and 5.0% were re-hospitalized due to heart insufficiency.

The plasma concentrations of CT-proET-1 in patients having a heart attack were increased as opposed to the normal range (median value: 44.3 pmol/l, range 10.5-77.4 pmol/l) at a median of 71 pmol/l range of 4.6-671 pmol/l. Compared to patients without any later events, the CT-proET-1 was higher in patients that later died, or that were re-hospitalized with heart insufficiency (median [range] pmol/l, 123.5; [14-671] vs. 74; [4.6-530; p<0.0001). NT-proBNP was also increased in patients having had events as opposed to patients without any later events (p<0.0001). Additional details are illustrated in Tables 1 and 2.

Figure 1:
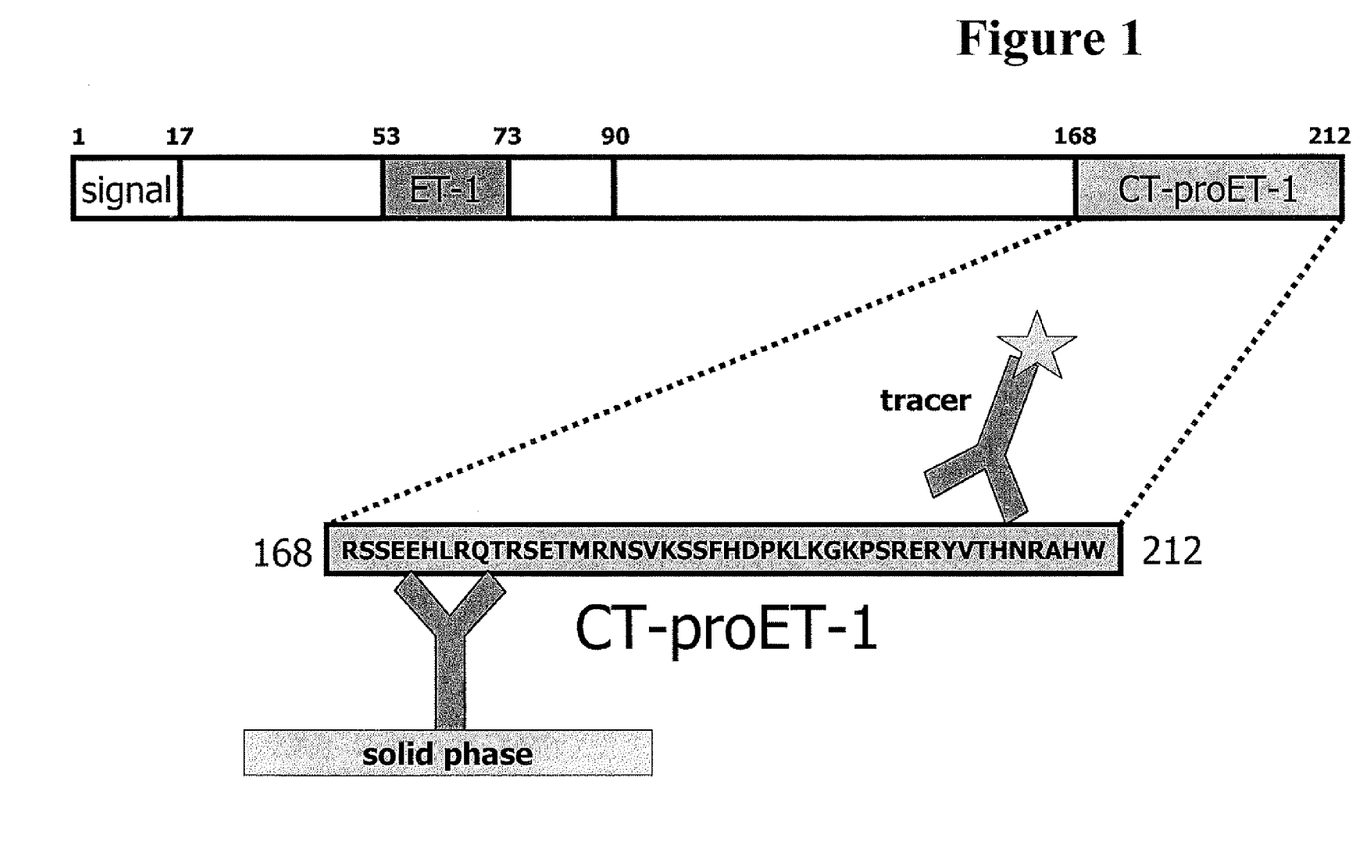
FIG. 1: Formula for the diagnostic availability of CT-proET SEQ ID No. 3 with the detection thereof by means of a probe (antibodies).
Figure 2:
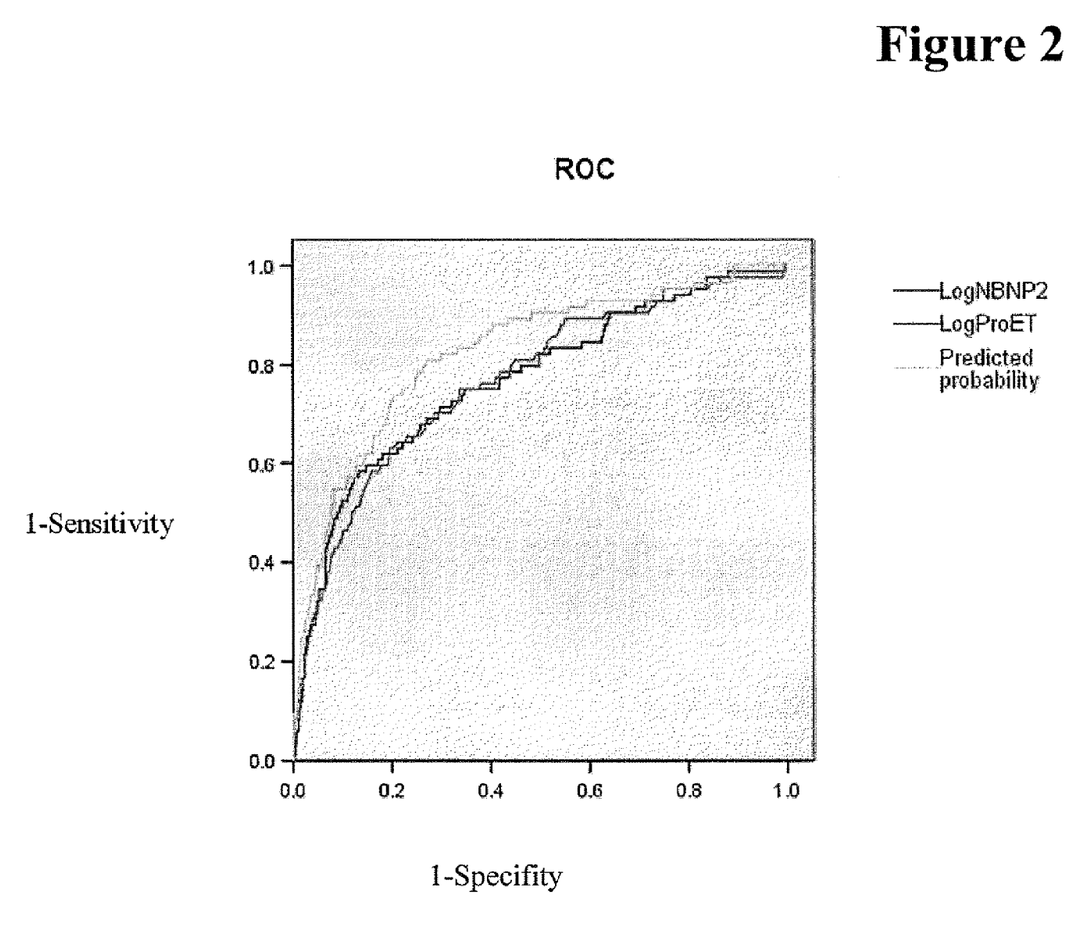
FIG. 2: ROC-curves for the prognosis of death/heart insufficiency by means of NT-proBNP or CT-proET-1, or from the combination of both parameters derived from the logistic regression model.

The Cox proportional hazards model for the prediction of death/heart insufficiency identified CT-proET-1 and NT-proBNP as independent predictors (log CT-proET-1 (HT 6.82), log NT-BNP (HR 2.661). The receiver-operating curve for CT-proET-1 resulted in an area under the curve (AUC) of 0.77 (95% CI: 0.71-0.83, p<0.001); for NT-proBNP the AUC was also 0.77 (95% CI: 0.71-0.83, p<0.001); the combination of both markers in the logistic model resulted in an AUC of 0.82 (95% CI: 0.77-0.87, p<0.001), also in a greater AUC than those of the two individual markers (FIG. 2).

Figure 3:
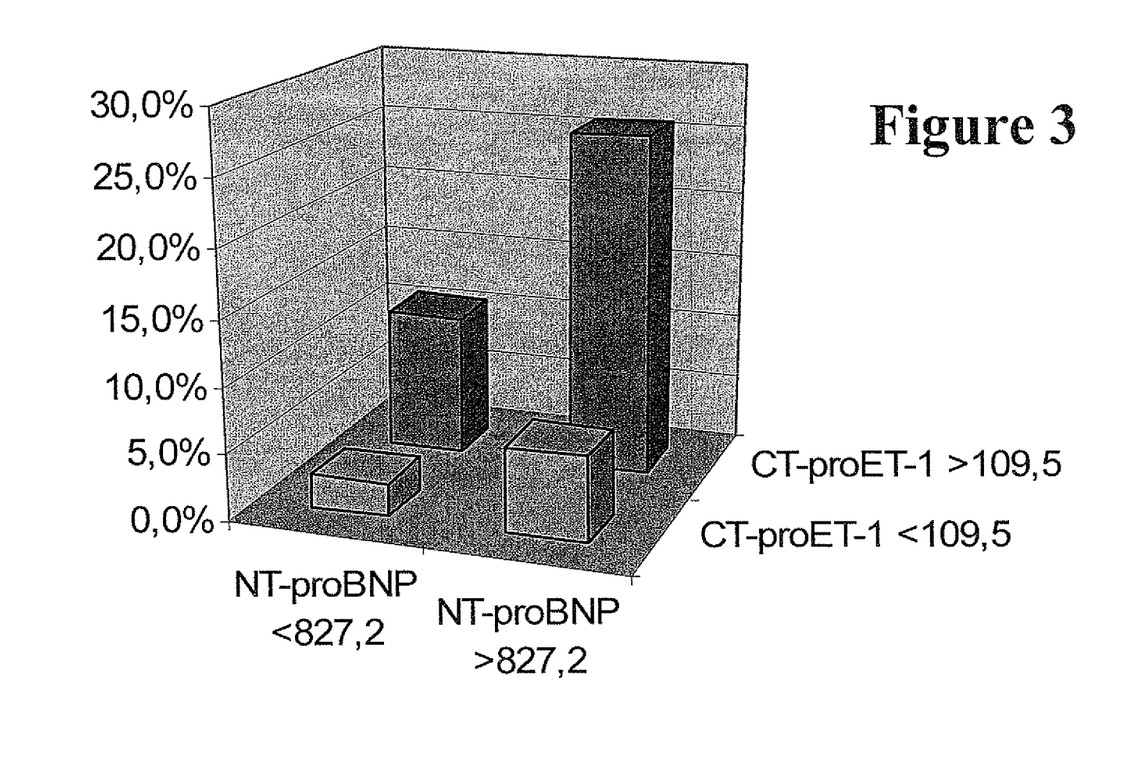
FIG. 3: Rate of the events (death, heart insufficiency) according to sub-grouping the heart attack patients according to the cut-off concentrations for CT-proET-1 and NT-pro BNP stated (both in pmol/l). The cut-off concentrations were each determined as those concentrations from the ROC analysis, in which the product of sensitivity and specificity was at a maximum for the event prognosis.
Figure 4:
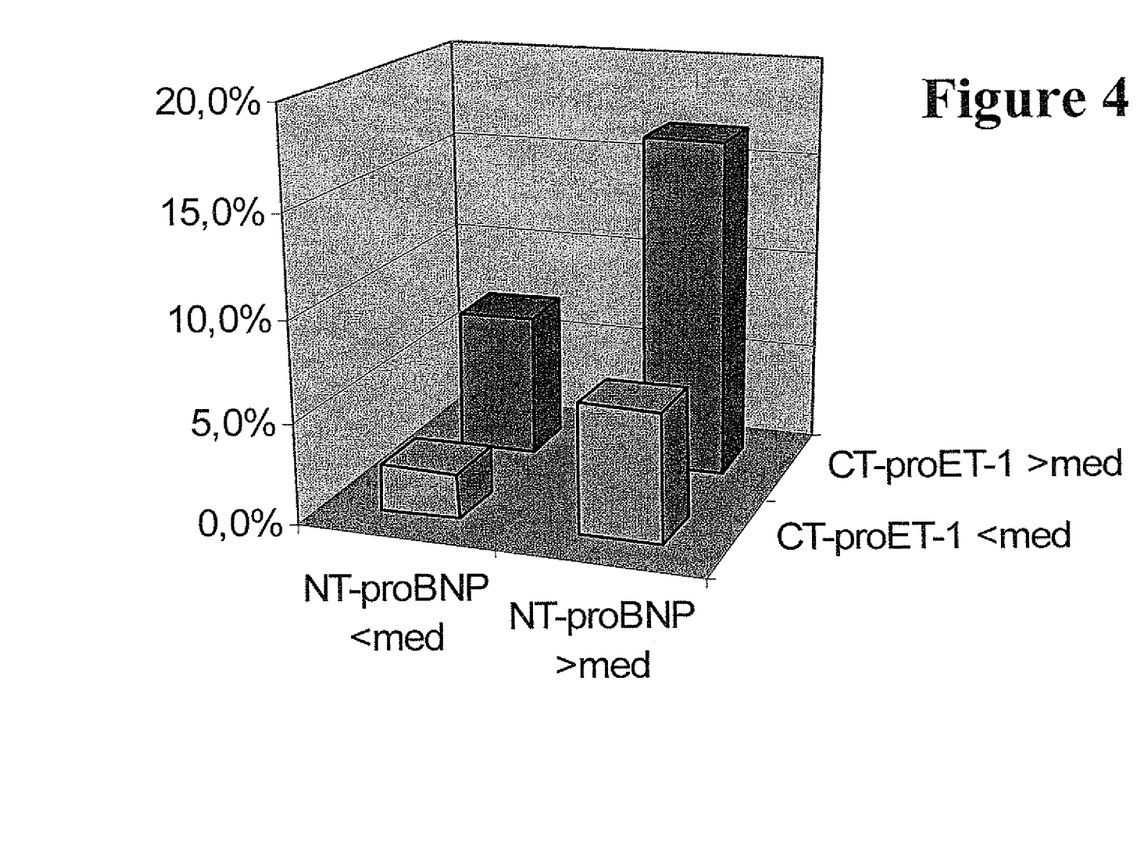
FIG. 4: Rate of the events (death, heart insufficiency) according to sub-grouping the heart attack patients according to the position of the measurement values for CT-proET-1 and NT-proBNP, based on the respective median of the measurement values of all heart attack patients. The median was 77 pmol/for CT-proET-1, and 914 pmol/l for NT-proBNP.

The additional benefit resulting from the combination of both markers CT-proET-1 and NT-proBNP as opposed to both individual markers is also illustrated in FIGS. 3 and 4, wherein an event rate of after 60 days is taken as the basis. The patients were classified according to cut-off-values, and the event rates obtained in the sub-groups obtained in this manner are illustrated. In FIG. 3 those concentrations were detected from the ROC analysis as cut-off-values, in which the product of sensitivity and specificity was at a maximum for the event prognosis. In FIG. 4 the medians of the entire patient populations serves as the cut-off value.

TABLE 1

Characteristics of the patients, separated into CT-proET-1 quartiles.

|  | $1^{st}$ quartile | $2^{nd}$ quartile | $3^{rd}$ quartile | $4^{th}$ quartile | p-value |
|---|---|---|---|---|---|
| Age (in years) | 58.9 ± 11.7 | 63.5 ± 11.7 | 65.9 ± 11.3 | 71.7 ± 10.7 | <0.0001 |
| Men | 202 (84.2) | 184 (75.7) | 168 (70.0) | 158 (64.8) | <0.0001 |
| Medical history |  |  |  |  |  |
| Acute myocardial infarction | 26 (10.8) | 40 (16.5) | 38 (15.8) | 60 (24.6) | 0.001 |
| Angina pectoris | 56 (23.3) | 62 (25.5) | 52 (21.7) | 79 (32.4) | 0.038 |
| Hypertension | 82 (24.2) | 106 (43.6) | 101 (42.1) | 131 (53.7) | <0.0001 |
| Diabetes mellitus | 34 (14.2) | 47 (19.3) | 51 (21.3) | 79 (32.4) | <0.0001 |
| High cholesterol | 47 (19.6) | 52 (21.4) | 66 (27.5) | 60 (24.6) | 0.176 |
| Smokers (former or current) | 149 (62.1) | 159 (65.4) | 162 (67.5) | 135 (55.3) | 0.030 |
| Acute myocardial infarction with elevation of ST segment | 196 (81.7) | 179 (72.8) | 209 (83.8) | 208 (80.3) | 0.284 |
| Thrombolytica | 143 (59.6) | 126 (51.9) | 143 (59.6) | 119 (48.8) | 0.034 |
| Region of infarction |  |  |  |  | 0.077 |
| Anterior | 105 (43.8) | 102 (42.0) | 102 (42.5) | 102 (41.8) |  |
| Inferior | 103 (42.9) | 89 (36.6) | 98 (40.8) | 83 (34.0) |  |
| Other | 32 (13.3) | 52 (21.4) | 40 (16.7) | 58 (23.8) |  |
| Killip class at admission |  |  |  |  | <0.0001 |
| I | 162 (67.5) | 132 (54.3) | 114 (46.3) | 84 (34.4) |  |
| II | 68 (28.3) | 93 (38.3) | 104 (43.3) | 109 (44.7) |  |
| III | 9 (3.8) | 14 (5.8) | 24 (10.0) | 41 (16.8) |  |
| IV | 1 (0.4) | 0 (0) | 0 (0) | 9 (3.7) |  |

TABLE 1-continued

Characteristics of the patients, separated into CT-proET-1 quartiles.

| | 1st quartile | 2nd quartile | 3rd quartile | 4th quartile | p-value |
|---|---|---|---|---|---|
| Peak CK (IU/L) | 838.5 ± 794.9 | 895.4 ± 1091.8 | 1261.5 ± 1243.1 | 1273.0 ± 1590.7 | <0.0001 |
| eGFR (ml/min/1.73 m2) | 76.9 ± 16.0 | 74.5 ± 16.1 | 67.7 ± 17.5 | 52.7 ± 18.5 | <0.0001 |
| NTproBNP (pmol/L) | 1031.6 ± 2267.7 | 1224.9 ± 1783.0 | 2141.5 ± 2400.5 | 4350.6 ± 3547.1 | <0.0001 |

The values are stated as median values (SD) or as figures (%).

TABLE 2

Comparison of CT-proET-1 and NT-proBNO Concentrations in different sub-groups of patients having acute myocardial infarction

| | Median CT-proET-1 (pmol/l) | p-value | Median NTproBNP (pmol/l) | p-value |
|---|---|---|---|---|
| Death vs. surviving | 126.0 vs. 74.0 | p < 0.0001 | 5929.3 vs. 802.4 | p < 0.0001 |
| Heart insufficiency vs. no event | 112 vs. 74.9 | p < 0.0001 | 3932.9 vs. 839.0 | p < 0.0001 |
| Female vs. male | 89.0 vs. 73.0 | p < 0.0001 | 788.7 vs. 1632.6 | p < 0.0001 |
| Previous AMI vs. no previous AMI | 85.0 vs. 75.0 | p < 0.0001 | 1332.3 vs. 844.4 | p < 0.001 |
| Hypertension vs. normotensive | 84.0 vs. 73.2 | p < 0.0001 | 1105.6 vs. 802.4 | p < 0.0001 |
| Previous heart insufficiency vs. no previous heart insufficiency | 108.0 vs. 75.9 | p < 0.0001 | 4160.1 vs. 856.6 | p < 0.0001 |
| STEMI vs. NSTEMI | 78.1 vs. 72.9 | p = NS | 1017.9 vs. 624.6 | p < 0.002 |
| Killip class over 1 vs. Killip class 1 | 88.9 vs. 70.0 | p < 0.0001 | 1595.1 vs. 631.5 | p < 0.0001 |

The invention claimed is:

1. A method for the in-vitro diagnosis or prognosis of acute coronary syndrome, or post-myocardial infarction, comprising
determining the level of CT-pro-ET-1 in at least one blood sample from a patient, wherein said CT-pro-ET-1 refers to SEQ ID NO: 2, or SEQ ID NO: 3, or both, and
determining the level of NT-proBNP (SEQ ID NO: 4) in said at least one blood sample from said patient,
wherein an increased level of CT-pro-ET-1 and an increased level of NT-proBNP in said at least one sample indicates the presence in said patient of acute coronary syndrome, or an increased risk of or an unfavorable prognosis of acute coronary syndrome or post-myocardial infarction for said patient.

2. The method for the diagnosis and/or risk classification of acute coronary syndrome, and/or post myocardial infarction according to claim 1, for identifying patients having an increased risk and/or an unfavorable prognosis of acute coronary syndrome, particularly myocardial infarction, Angina pectoris, and/or post-myocardial infarction.

3. The method for the diagnosis and/or risk classification of acute coronary syndrome, and/or post-myocardial infarction according to claim 1, wherein the patient is a symptomatic and/or asymptomatic patient, particularly an emergency room patient.

4. The method for the diagnosis and/or risk classification of acute coronary syndrome, and/or post-myocardial infarction according to claim 1 for the therapy control of acute coronary syndrome, particularly myocardial infarction (AMI) and Angina pectoris (AP), and/or post-myocardial infarction, particularly in intensive medicine or emergency medicine.

5. The method for the diagnosis and/or risk classification of acute coronary syndrome, and/or post-myocardial infarction according to claim 1 for carrying out clinical decisions, particularly the continuative treatment and therapy by means of pharmaceuticals, particularly in intensive medicine or emergency medicine, including the decision for hospitalizing the patient.

6. The method for the diagnosis and/or risk classification of acute coronary syndrome, and/or post-myocardial infarction according to claim 1 for the prognosis, for the differential diagnostic early detection and recognition, for the assessment of the degree of severity, and for the therapy-accompanying assessment of the course.

7. The method according to claim 1, characterized in that the cut-off values are 80-150 pmol/l for CT-proET-1, and 750-1100 pmol/l for NT-proBNP.

8. The method according to claim 1, characterized in that additionally a determination of at least one further marker is carried out, which is selected from the group of inflammatory markers, cardiovascular markers, neurohormonal markers, or ischemic markers.

9. The method according to claim 8, characterized in that the inflammatory marker is selected from at least one marker of the group of C-reactive protein (CRP), cytokins, such as TNF-alpha, interleukins, such as IL-6, procalcitonin (1-116, 3-116), and adhesion molecules, such as VCAM or ICAM.

10. The method according to claim 8, characterized in that the cardiovascular marker is selected from the group of creatine kinasis, myoglobin, myeloperoxidasis, natriuretic protein, particularly ANP (or ANF), proANP, NT-proANP, BNP, pro-BNP, or a partial sequence thereof, cardial roponin, CRP, and circulation regulating (pro)hormones, such as pro-gastrin-releasing peptide (proGRP), pro-endothelin-1, pro-leptin, pro-neuropeptide-Y, pro-somatostatin, pro-neuropeptide-YY, pro-opiomelanocortin, or pro-adrenomedullin (proADM), or a partial sequence thereof.

11. The method according to claim 8, characterized in that the ischemic marker is selected from at least one marker of the group of troponin I and T, CK-MB.

12. The method according to claim 8, characterized in that the neurohormonal marker is at least one natriuretic protein, particularly ANP (or ANF), proANP, NT-proANP, BNP, proBNP, or a partial sequence thereof.

13. The method according to claim 1, characterized in that the parallel or simultaneous determinations of the marker are to be carried out.

14. The method according to claim 1, characterized in that the determinations are carried out on at least one patient sample.

15. The method according to claim 1, characterized in that the determinations are carried out on an automatic analysis device, particularly by means of a Kryptor.

16. The method according to claim 1, characterized in that the determinations are carried out by means of a quick test, particularly in single or multiple parameter determinations.

17. A kit for the risk classification of acute coronary syndrome, myocardial infarction, Angina pectoris, and/or post-myocardial infarction containing detection reagents for determining CT-proET 1, wherein said CT-pro-ET-1 refers to SEQ ID NO: 2, or SEQ ID NO: 3, or both, in combination with NT-proBNP (SEQ ID No. 4) and optionally further markers according to claim 8, and auxiliary means.

18. A diagnostic device for carrying out a method according to claim 1.

19. The kit for the diagnosis of acute coronary syndrome, myocardial infarction, and/or Angina pectoris, containing detection reagents for determining CT-proET-1, wherein said CT-pro-ET-1 refers to SEQ ID NO: 2, or SEQ ID NO: 3, or both, in combination with NT-proBNP (SEQ ID No. 4) and optionally further markers according to claim 8, and auxiliary means.

20. The method according to claim 7, characterized in that the cut-off values are 90-130 pmol/l for CT-proET-1, and 800-950 pmol/l for NT-proBNP.

* * * * *

SEQUENCE LISTING

<160> NUMBER OF SEQ ID NOS: 4

<210> SEQ ID NO 1
<211> LENGTH: 212
<212> TYPE: PRT
<213> ORGANISM: Human

<400> SEQUENCE: 1

Met Asp Tyr Leu Leu Met Ile Phe Ser Leu Leu Phe Val Ala Cys Gln
1               5                   10                  15

Gly Ala Pro Glu Thr Ala Val Leu Gly Ala Glu Leu Ser Ala Val Gly
            20                  25                  30

Glu Asn Gly Gly Glu Lys Pro Thr Pro Ser Pro Pro Trp Arg Leu Arg
        35                  40                  45

Arg Ser Lys Arg Cys Ser Cys Ser Ser Leu Met Asp Lys Glu Cys Val
    50                  55                  60

```
Tyr Phe Cys His Leu Asp Ile Ile Trp Val Asn Thr Pro Glu His Val
 65                  70                  75                  80

Val Pro Tyr Gly Leu Gly Ser Pro Arg Ser Lys Arg Ala Leu Glu Asn
                 85                  90                  95

Leu Leu Pro Thr Lys Ala Thr Asp Arg Glu Asn Arg Cys Gln Cys Ala
            100                 105                 110

Ser Gln Lys Asp Lys Lys Cys Trp Asn Phe Cys Gln Ala Gly Lys Glu
        115                 120                 125

Leu Arg Ala Glu Asp Ile Met Glu Lys Asp Trp Asn Asn His Lys Lys
130                 135                 140

Gly Lys Asp Cys Ser Lys Leu Gly Lys Lys Cys Ile Tyr Gln Gln Leu
145                 150                 155                 160

Val Arg Gly Arg Lys Ile Arg Arg Ser Ser Glu Glu His Leu Arg Gln
                165                 170                 175

Thr Arg Ser Glu Thr Met Arg Asn Ser Val Lys Ser Ser Phe His Asp
            180                 185                 190

Pro Lys Leu Lys Gly Lys Pro Ser Arg Glu Arg Tyr Val Thr His Asn
        195                 200                 205

Arg Ala His Trp
    210

<210> SEQ ID NO 2
<211> LENGTH: 120
<212> TYPE: PRT
<213> ORGANISM: Human

<400> SEQUENCE: 2

Ala Leu Glu Asn Leu Leu Pro Thr Lys Ala Thr Asp Arg Glu Asn Arg
 1               5                  10                  15

Cys Gln Cys Ala Ser Gln Lys Asp Lys Lys Cys Trp Asn Phe Cys Gln
                 20                  25                  30

Ala Gly Lys Glu Leu Arg Ala Glu Asp Ile Met Glu Lys Asp Trp Asn
             35                  40                  45

Asn His Lys Lys Gly Lys Asp Cys Ser Lys Leu Gly Lys Lys Cys Ile
 50                  55                  60

Tyr Gln Gln Leu Val Arg Gly Arg Lys Ile Arg Arg Ser Ser Glu Glu
 65                  70                  75                  80

His Leu Arg Gln Thr Arg Ser Glu Thr Met Arg Asn Ser Val Lys Ser
                 85                  90                  95

Ser Phe His Asp Pro Lys Leu Lys Gly Lys Pro Ser Arg Glu Arg Tyr
            100                 105                 110

Val Thr His Asn Arg Ala His Trp
        115                 120

<210> SEQ ID NO 3
<211> LENGTH: 45
<212> TYPE: PRT
<213> ORGANISM: Human

<400> SEQUENCE: 3

Arg Ser Ser Glu Glu His Leu Arg Gln Thr Arg Ser Glu Thr Met Arg
 1               5                  10                  15

Asn Ser Val Lys Ser Ser Phe His Asp Pro Lys Leu Lys Gly Lys Pro
                 20                  25                  30

Ser Arg Glu Arg Tyr Val Thr His Asn Arg Ala His Trp
             35                  40                  45
```

```
<210> SEQ ID NO 4
<211> LENGTH: 76
<212> TYPE: PRT
<213> ORGANISM: Human

<400> SEQUENCE: 4

His Pro Leu Gly Ser Pro Gly Ser Ala Ser Asp Leu Glu Thr Ser Gly
1               5                   10                  15

Leu Gln Glu Gln Arg Asn His Leu Gln Gly Lys Leu Ser Glu Leu Gln
            20                  25                  30

Val Glu Gln Thr Ser Leu Glu Pro Leu Gln Glu Ser Pro Arg Pro Thr
            35                  40                  45

Gly Val Trp Lys Ser Arg Glu Val Ala Thr Glu Gly Ile Arg Gly His
    50                  55                  60

Arg Lys Met Val Leu Tyr Thr Leu Arg Ala Pro Arg
65                  70                  75
```